(12) United States Patent
Lee (10) Patent No.: US 9,770,226 B2
(45) Date of Patent: Sep. 26, 2017

(54) METHOD AND APPARATUS FOR REPRESENTING PRESSURE VARIATION IN OBJECT

(71) Applicant: SAMSUNG MEDISON CO., LTD., Gangwon-Do (KR)

(72) Inventor: Jin-yong Lee, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 155 days.

(21) Appl. No.: 14/566,362

(22) Filed: Dec. 10, 2014

(65) Prior Publication Data

US 2015/0257736 A1 Sep. 17, 2015

(30) Foreign Application Priority Data

Mar. 13, 2014 (KR) .................. 10-2014-0029763

(51) Int. Cl.
| | | |
|---|---|---|
| *A61B 8/00* | (2006.01) | |
| *A61B 8/04* | (2006.01) | |
| *A61B 8/08* | (2006.01) | |
| *A61B 8/06* | (2006.01) | |

(52) U.S. Cl.
CPC .............. *A61B 8/463* (2013.01); *A61B 8/04* (2013.01); *A61B 8/0883* (2013.01); *A61B 8/0891* (2013.01); *A61B 8/469* (2013.01); *A61B 8/5223* (2013.01); *A61B 8/065* (2013.01); *A61B 8/488* (2013.01)

(58) Field of Classification Search
CPC .. A61B 8/04; A61B 8/065; A61B 8/08; A61B 8/0883; A61B 8/488; A61B 8/5223
See application file for complete search history.

(56) References Cited

U.S. PATENT DOCUMENTS

| | | | |
|---|---|---|---|
| 2010/0286522 A1* | 11/2010 | Beach ................ | A61B 5/02007 600/441 |
| 2012/0041313 A1 | 2/2012 | Tanaka et al. | |
| 2013/0137987 A1 | 5/2013 | Abe et al. | |
| 2013/0245441 A1* | 9/2013 | Datta ....................... | A61B 8/13 600/438 |
| 2014/0236008 A1 | 8/2014 | Tanaka et al. | |

FOREIGN PATENT DOCUMENTS

| | | |
|---|---|---|
| EP | 2514368 A1 | 10/2012 |
| JP | 2012-110527 A | 6/2012 |
| WO | 20131057999 A1 | 4/2013 |

OTHER PUBLICATIONS

Strauss, A. L., et al. "Noninvasive Assessment of Pressure Gradients Across Iliac Artery Stenoses: Duplex and Catheter Correlative Study," Journal of Ultrasound in Medicine. 1993. vol. 12, p. 17-22 (XP-001040847).

Extended European Search Report issued in corresponding European Patent Application No. 14174908.5, mailed on Aug. 11, 2015.

* cited by examiner

*Primary Examiner* — Joel Lamprecht
(74) *Attorney, Agent, or Firm* — McDermott Will & Emery LLP (57) ABSTRACT

Provided is a method of representing a pressure variation in an object on an image of the object. The method includes: measuring all velocity components of the object; selecting a first position on the image of the object; estimating a pressure variation between the first position and a second position that is separate from the selected first position; and displaying an estimated pressure variation on the image of the object by using a predetermined indicator.

15 Claims, 6 Drawing Sheets

METHOD AND APPARATUS FOR REPRESENTING PRESSURE VARIATION IN OBJECT

RELATED APPLICATIONS

This application claims the benefit of Korean Patent Application No. 10-2014-0029763, filed on Mar. 13, 2014, in the Korean Intellectual Property Office, the disclosure of which is incorporated herein in its entirety by reference.

BACKGROUND

1. Field

One or more embodiments of the present invention relate to a method and apparatus for representing a pressure variation in an object, and more particularly, to a method and apparatus for representing a relative pressure variation in an object at predetermined points on an image of the object.

2. Description of the Related Art

An ultrasound diagnosis apparatus transmits an ultrasound signal from a body surface of an object to a target region in the body and acquires an image of soft tissue tomography or blood flow by using information on an ultrasound signal reflected from tissue in the body.

An ultrasound diagnosis apparatus irradiates an ultrasound signal generated by a transducer of a probe onto an object and receives information on an echo signal reflected from the object to acquire an image of an interior region of the object. Such an ultrasound diagnosis apparatus may display information on the object in real time. Furthermore, an ultrasound diagnosis apparatus has high safety because an object is not exposed to X-ray radiation. Hence, an ultrasound diagnosis apparatus is widely used along with other image diagnosis apparatuses, such as an X-ray diagnosis apparatus, a computerized tomography (CT) scanner, a magnetic resonance imaging (MRI) machine, and a nuclear medicine diagnosis apparatus.

SUMMARY

One or more embodiments of the present invention include a method and apparatus for representing a pressure variation in an object.

Additional aspects will be set forth in part in the description which follows and, in part, will be apparent from the description, or may be learned by practice of the presented embodiments.

According to one or more embodiments of the present invention, a method of representing a pressure variation in an object on an image of the object includes: measuring all velocity components of the object; selecting a first position on the image of the object; estimating a pressure variation between the first position and a second position that is separate from the selected first position; and displaying an estimated pressure variation on the image of the object by using a predetermined indicator.

The object may be a blood vessel or a heart, and the measuring of all the velocity components of the object may include acquiring velocity components at respective positions of an interior of the object.

The measuring of all the velocity components of the object may include acquiring velocity components at respective positions of an interior of the object by using plane waves.

The first position may be a predetermined point or region of the interior of the object.

The estimating of a pressure variation between the first position and a second position that is separate from the selected first position may include estimating a pressure variation value ($\Delta p$) at the second position with respect to the first position, based on the velocity component at the first position and the velocity component at the second position.

The pressure variation value $\Delta p$ may be estimated by using $\Delta P = 4*(v_2^2 - v_1^2)$.

The predetermined indicator may include at least one of characters, numbers, symbols, colors, graphs, and images.

According to one or more embodiments of the present invention, an apparatus for representing a pressure variation in an object on an image of the object includes: a velocity component measurement unit that measures all velocity components of the object; a position selection unit that selects a first position on the image of the object; a pressure variation estimation unit that estimates a pressure variation between the first position and a second position that is separate from the selected first position; and a display unit that displays an estimated pressure variation on the image of the object by using a predetermined indicator.

The object may be a blood vessel or a heart, and the velocity component measurement unit may acquire velocity components at respective positions of an interior of the object.

The velocity component measurement unit may acquire velocity components at respective positions of an interior of the object by using plane waves.

The first position may be a predetermined point or region of the interior of the object.

The pressure variation estimation unit may estimate a pressure variation value ($\Delta p$) at the second position with respect to the first position, based on the velocity component at the first position and the velocity component at the second position.

The pressure variation value $\Delta p$ may be estimated by using $\Delta P = 4*(v_2^2 - v_1^2)$.

The predetermined indicator may include at least one of characters, numbers, symbols, colors, graphs, and images.

According to one or more embodiments of the present invention, there is provided a computer-readable recording medium that stores a program, which, when executed by a computer, performs one of the above-described methods.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

The terms used herein will be briefly described prior to the detailed description of embodiments of the present invention.

As the terms used herein, so far as possible, the most widely used terms are selected in consideration of functions in the embodiments; however, these terms may vary according to the intentions of those skilled in the art, the precedents, or the appearance of new technology. Some terms used herein may be arbitrarily chosen by the present applicant. In this case, these terms will be defined in detail below. Accordingly, the specific terms used herein should be understood based on the unique meanings thereof and the whole context of the present invention.

It will also be understood that the terms "comprises", "includes", and "has", when used herein, specify the presence of stated elements, but do not preclude the presence or addition of other elements, unless otherwise defined. Also, the terms "unit" and "module" used herein represent a unit for processing at least one function or operation, which may be implemented by hardware, software, or a combination of hardware and software.

Throughout the specification, the term "ultrasound image" refers to an image of an object, which is acquired by using ultrasound waves.

The term "object" may refer to a part of a body. For example, the object may include an organ, such as a liver, a heart, a womb, a brain, a breast, and an abdomen, or a fetus. The object may include a phantom. The phantom may refer to a material having a volume that is very approximate to the density and effective atomic number of a living body.

In addition, throughout the specification, the term "user" may refer to a medical expert, such as a doctor, a nurse, a medical technologist, a medical image expert, and a technician who repairs medical equipment, but is not limited thereto.

Embodiments of the present invention will be described below in detail with reference to the accompanying drawings so that those of ordinary skill in the art may easily implement the present invention. The invention may, however, be embodied in many different forms and should not be construed as being limited to the embodiments set forth herein. In addition, portions irrelevant to the description of the embodiments of the present invention will be omitted in the drawings for a clear description of the embodiments of the present invention, and like reference numerals will denote like elements throughout the specification.

A flow, such as blood flow, occurs due to a pressure difference. The pressure difference may be calculated by using a Doppler effect. A diagnosis or analysis may be hemodynamically performed on an object by using the pressure difference. The present invention may allow a user to grasp an entire pressure variation in an object at a glance by using an image of a pressure variation, thus making a diagnosis of the object quickly and precisely. For example, vascular closure, normality, and abnormality in heart valves, and so on may be easily determined through a blood flow analysis using an image of a pressure difference.

Figure 1:
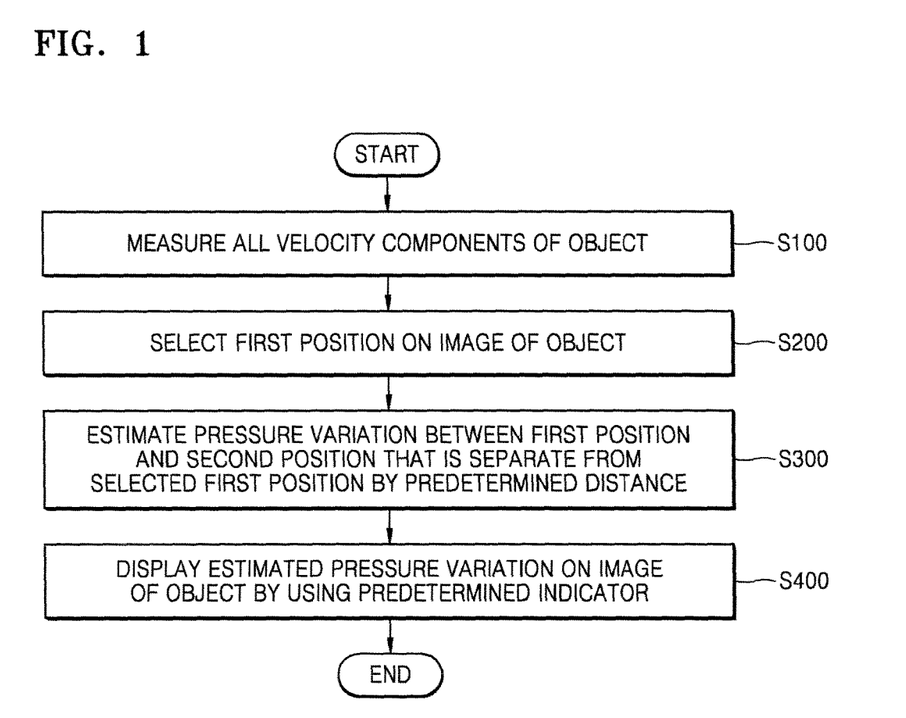
FIG. 1 is a flowchart of a method of representing a relative pressure variation in an object, according to an embodiment of the present invention.

FIG. 1 is a flowchart of a method of representing a relative pressure variation in an object on an image of the object, according to an embodiment of the present invention.

The method of representing the pressure variation in the object on the image of the object, according to the embodiment of the present invention, may include measuring all velocity components of the object (S100), selecting a first position on an image of the object (S200), estimating a pressure variation between the first position and a second position that is separate from the selected first position (S300), and displaying the estimated pressure variation on the image of the object by using a predetermined indicator (S400).

The measuring of all velocity components of the object (S100) may include acquiring velocity components at respective positions of the interior of the object. The velocity components at respective positions of the object may be acquired by using the well-known Doppler method.

In addition, the measuring of all velocity components of the object (S100) may include acquiring velocity components for an entire region of the object by using, for example, multicouple volume Doppler technology based on ultrasound data obtained through plane waves transmitted and received with respect to the object. By using the plane waves, the velocity components of all the points of the object may be acquired. In addition, by using multicouple volume Doppler technology, velocity components between multipoints may be calculated. In order words, the measuring of all velocity components of the object (S100) may include acquiring velocity components at respective positions of the interior of the object by using the plane waves at one time.

According to an embodiment of the present invention, the velocity components for the object are acquired at one time by using plane waves, and a relative pressure at a point or region of the object may be estimated based on the acquired velocity components. According to the embodiment of the present invention, the relative pressure of the object may be estimated quickly and precisely.

According to an embodiment of the present invention, the object may be a blood vessel or a heart.

According to the embodiment of the present invention, the selecting of the first position on the image of the object (S200) may include selecting the first position on the image of the object through a predetermined external input obtained through, for example, a user input unit (not illustrated).

The first position according to the embodiment may be a predetermined point or region of the interior of the object. For example, when the object is a blood vessel, a predetermined point of the interior of the blood vessel may be selected as the first position. In addition, a region including a predetermined cross-section of the blood vessel, for example, a transverse section or a longitudinal section may be selected as the first position.

The first position as described above may be included in a current ultrasound image of the object which a user is looking at or in a previous ultrasound image of the object. For example, the first position may be included in an ultrasound image of the blood vessel which the user is currently looking at. The first position may be included in a previous frame of the ultrasonic image which the user is currently looking at.

According to the embodiment of the present invention, the estimating of the pressure variation between the first position and the second position that is separate from the selected first position may include estimating a pressure variation value Δp at the second position with respect to the first position, based on the velocity component at the first position and the velocity component at the second position.

For example, a relative pressure variation at the second position with respect to the first position may be estimated by using the velocity component at the first position and the velocity component at the second position. According to the embodiment, the pressure variation value Δp may be estimated by using $\Delta P = 4*(v_2^2 - v_1^2)$. A relevant description will be given with reference to FIGS. 2 and 3A to 3C.

In addition, the method according to the embodiment of the present invention may include displaying the pressure variation that is estimated through operation S300 on the image of the object by using a predetermined indicator (S400). According to the embodiment of the present invention, the predetermined indicator may include at least one of characters, numbers, symbols, colors, graphs, and images.

Figure 2:
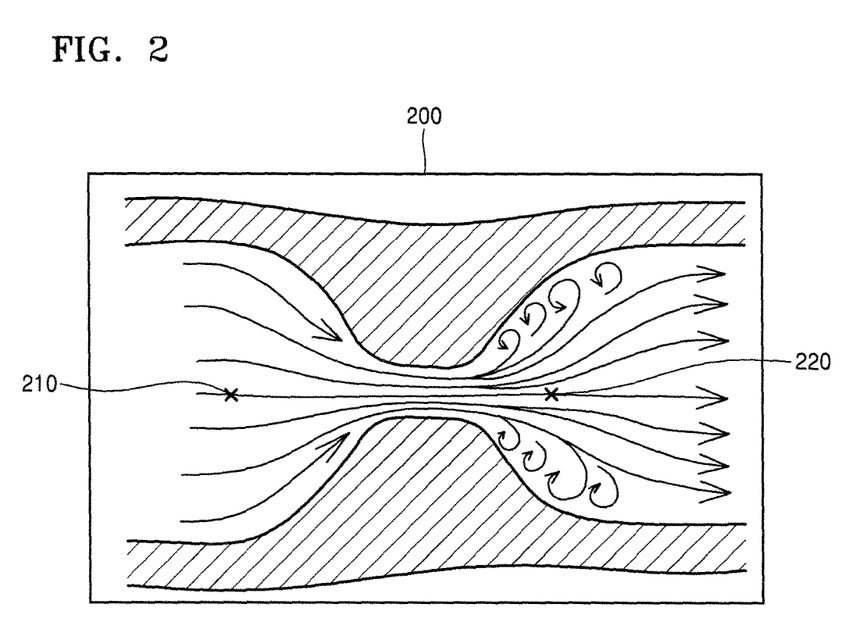
FIG. 2 illustrates a method of estimating a relative pressure variation at respective positions of an object, based on measured velocity components, according to an embodiment of the present invention.

FIG. 2 illustrates a method of estimating a relative pressure variation at respective positions of an object, based on measured velocity components.

According to the embodiment of the present invention, when all velocity components of the object are measured, a pressure variation may be estimated by using Equation 1.

$$p_1 - p_2 = 1/2\rho(v_2^2 - v_1^2) + \rho \int_1^2 \frac{d\vec{v}}{dt}\vec{ds} + R(\vec{v})$$ Equation 1

Equation 1 may include a convective acceleration (for example, $\frac{1}{2}\rho(v_2^2 - v_1^2)$), a flow acceleration (for example, $$\rho \int_1^2 \frac{d\vec{v}}{dt}\vec{ds}),$$

and a viscous friction (for example, $R(\vec{v})$). In Equation 1, P1 denotes a pressure at a first position, and P2 denotes a pressure at a second position. Referring to FIG. 2 that illustrates a blood vessel, P1 may be a pressure at a first position 210 of the interior of the object and P2 may be a pressure at a second position 220. Furthermore, ρ denotes a mass density of blood, for example, $1.06 \times 10^3$ kg/m³, v1 may denote a velocity value at the first point (for example, 210), and v2 may denote a velocity value at the second point (for example, 220).

Under a normal case of measuring pressure, the flow acceleration and the viscous friction may be ignored in Equation 1. Therefore, Equation 1 may be simply expressed as Equation 2.

$$\Delta P = 4*(v_2^2 - v_1^2)$$ Equation 2

In order words, a pressure variation value may be an integer multiple (for example, four times) of a difference between the squares of the velocity components at respective positions.

By using Equations 1 and 2 according to the embodiment of the present invention, relative pressure variations at respective positions of the object may be quickly and precisely acquired based on a velocity of blood flow of the object. In order words, by estimating a pressure variation according to a variation in the velocity of blood flow by using Bernoulli's equation as in Equation 1 rather than determining the pressure variation based on a variation in diameter of a blood vessel in the related art, information on a relative variation in blood pressure at each point of the object may be quickly and precisely acquired.

Figure 3A:
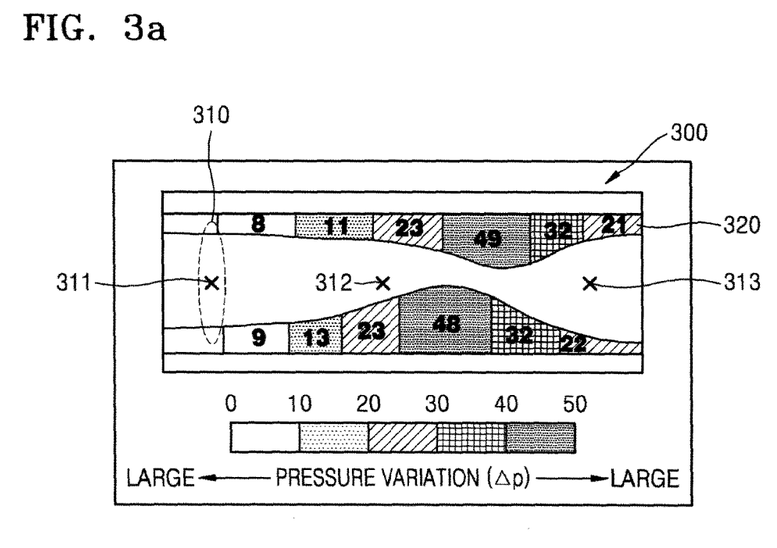
FIGS. 3A to 3C illustrate examples of a representation of a pressure variation in an object, according to embodiments of the present invention.
Figure 3B:
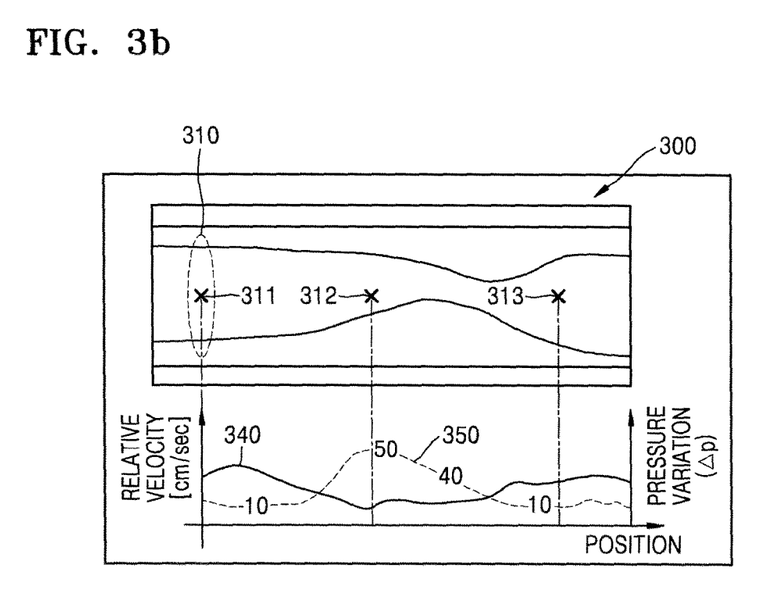
Figure 3C:
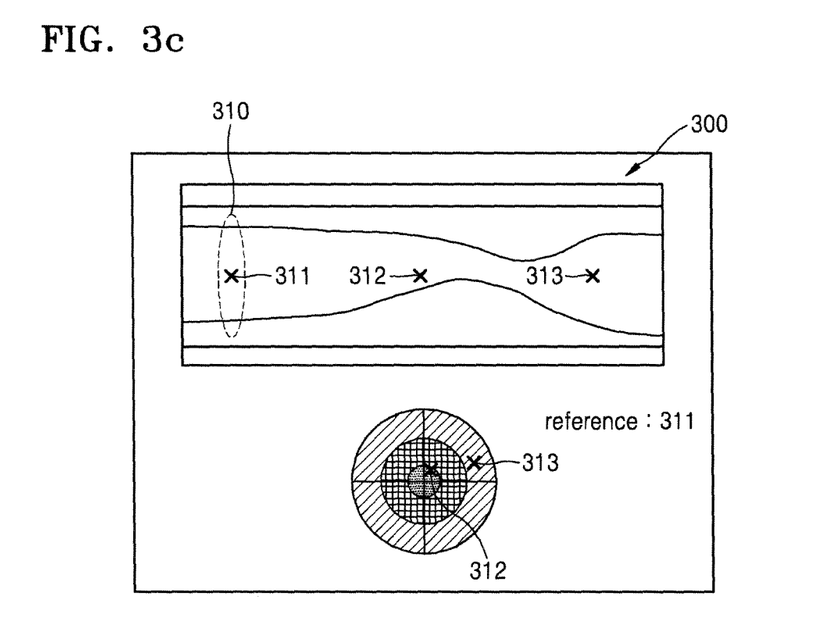

FIGS. 3A to 3C illustrate examples of a representation of a pressure variation in an object, according to an embodiment of the present invention.

FIG. 3A illustrates an example of a representation of a pressure variation in an object, according to an embodiment of the present invention. When the object is a blood vessel, an ultrasound image 300 of the blood vessel may be displayed as illustrated in FIG. 3A. All velocity components of the blood vessel may be measured by using a Doppler method. A predetermined region 310 of the ultrasound image 300 may be selected as a first position. For example, a predetermined cross-section 310 of the blood vessel as seen on the ultrasound image 300 may be selected as the first position. Alternatively, a predetermined cross-section (not illustrated) of the blood vessel that is not seen on the ultrasound image currently may be selected as the first position. According to the embodiment, the first position may include a predetermined point 311. For example, the predetermined point 311 included in the predetermined region 310 may be selected as the first position.

A second position that is separate from the first position 310 or 311 by a predetermined distance may be selected. For example, a predetermined point 312 or 313 inside the blood vessel may be selected as the second position. A region of interest (not illustrated) outside the blood vessel may be selected as the second position.

According to the embodiment, a pressure variation at the second position (for example, 312 or 313) that is separate from the first position 310 or 311 by the predetermined distance may be estimated. In order words, a pressure variation value at the second position with respect to the first position may be estimated by using Equation 2.

The estimated pressure variation value may be displayed on the ultrasound image 300 by using a predetermined indicator including characters, numbers, symbols, colors, graphs, or images. For example, as illustrated in FIG. 3A, the relative pressure variation value on a blood vessel wall 320 with respect to the first position 310 or 311 may be represented through a predetermined color by using a color bar in which different colors are assigned depending on the pressure variation. For example, when a blood vessel becomes narrow due to, for example, deposits, the pressure thereof increases, resulting in an increase in the pressure variation. Therefore, a color assigned to represent that a pressure variation is large at a portion at which the blood vessel becomes narrow may be displayed on the blood vessel wall 320. The pressure variation may be represented by a numerical value. As illustrated in FIG. 3A, when the pressure variation value is 8 or 9, the pressure variation is small, and when the pressure variation value is 48 or 49, the pressure variation is large.

FIG. 3B illustrates an example of a representation of a pressure variation in an object, according to another embodiment of the present invention. As described with reference to FIG. 3A, velocity components may be acquired at respective positions of the object including a second position (for example, 312 or 313) with respect to the first position 310 or 311. The velocity components at respective positions of the object may be represented by a graph 340 illustrated in FIG. 3B. When a portion of a blood vessel is narrow compared with the first position 310 or 311 that is a reference position, a velocity component of blood flow may decrease (for example, a velocity value at the point 312).

Similarly, a pressure variation or a pressure variation value Δp at each of the positions of the object with respect to the first position 310 or 311 may be estimated by using a graph 340 showing the velocity component at the first position 310 and 311 and the velocity component at the second position. The respective positions of the object with respect to the first position 310 or 311 may include the second position. The pressure variation value Δp may be represented by a graph 350 illustrated in FIG. 3B. Alternatively, the pressure variation value may be represented by numerical values on the graph 350 (for example, 10, 40, 50, etc.).

FIG. 3C illustrates an example of a representation of a pressure variation in an object, according to another embodiment of the present invention. As described with reference to FIG. 3A, velocity components may be acquired at respective positions of the object including the second position (for example, 312 or 313) with respect to the first position 310 or 311 and a pressure variation value may be estimated based on the velocity components. When a predetermined point 311 is selected as the first position, a pressure variation value at the second position (for example, 312 or 313) may be represented on a predetermined indicator having the form of a dart board. As illustrated in FIG. 3C, the center of the dart board represents a large pressure variation and the pressure variation decreases from the center toward the edges of the dart board. Since the pressure variation at the point 312 is larger than that at the predetermined point 311 that is the reference position, the pressure variation at the point 312 may be displayed on the center of the dart board. Since the pressure variation at the point 313 is small, the pressure variation at the point 313 may be displayed on the edge of the dart board that is far from the center as compared to the point 312.

Therefore, the user quickly and precisely ascertains at which portion a pressure variation is large, based on the indicator representing the pressure variation on an ultrasound image of the object.

Figure 4:
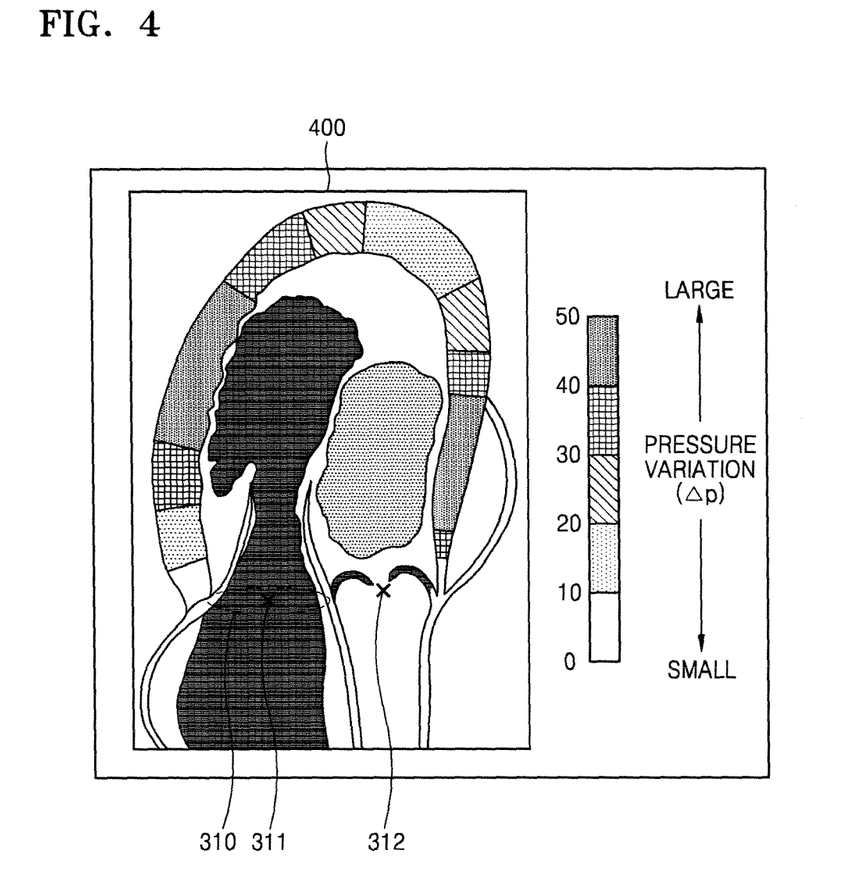
FIG. 4 illustrates an example of a representation of a pressure variation in an object, according to another embodiment of the present invention.

FIG. 4 illustrates a representation of a pressure variation in an object, according to another embodiment of the present invention.

According to the embodiment of the present invention, when the object is a heart, a heart ultrasound image 400 as illustrated in FIG. 4 may be obtained. Blood within the heart circulates from the body to the inside or outside of the heart due to the motion of the heart. A pressure variation may occur in a wall of the heart due to blood circulation within the heart. For example, when blood flows into the heart, a pressure variation may occur in a wall of the heart due to blood that contacts the wall of the heart.

Referring to FIG. 4, velocity components at respective positions of the object including the second position (for example, 312) may be acquired with respect to the first position 310 or 311 as described above. The velocity component may include a blood flow velocity component. A pressure variation value may be estimated based on the acquired velocity components at the respective positions of the object. Referring to FIG. 4, when blood flows into a heart by opening of the valves of the heart, a pressure variation at a portion of a wall of the heart at which blood first contacts may be large with respect to the first position 310 or 311. The pressure variation at the wall of the heart may be represented by using a color bar in which predetermined colors are assigned according to a pressure variation value. For example, a portion at which the pressure variation is largest (for example, a portion of the wall of the heart at which inflowing or outflowing blood first contacts) may be represented by a red color, and a portion at which the pressure variation is smallest may be represented by a blue color.

According to the embodiment of the present invention, a plurality of first positions or a plurality of second positions may be selected. According to the selected first position, pressure variations at the second positions may be represented in different forms. For example, a predetermined region 310 or a predetermined point 311 may be selected as the first position. The pressure variation at the predetermined region 310 may be represented as illustrated in FIG. 3A, and the pressure variation at the predetermined point 311 may be represented as illustrated in FIG. 3B. The second position may include an inside or outside region or point of the object, which may also be referred to as a region of interest.

Figure 5:
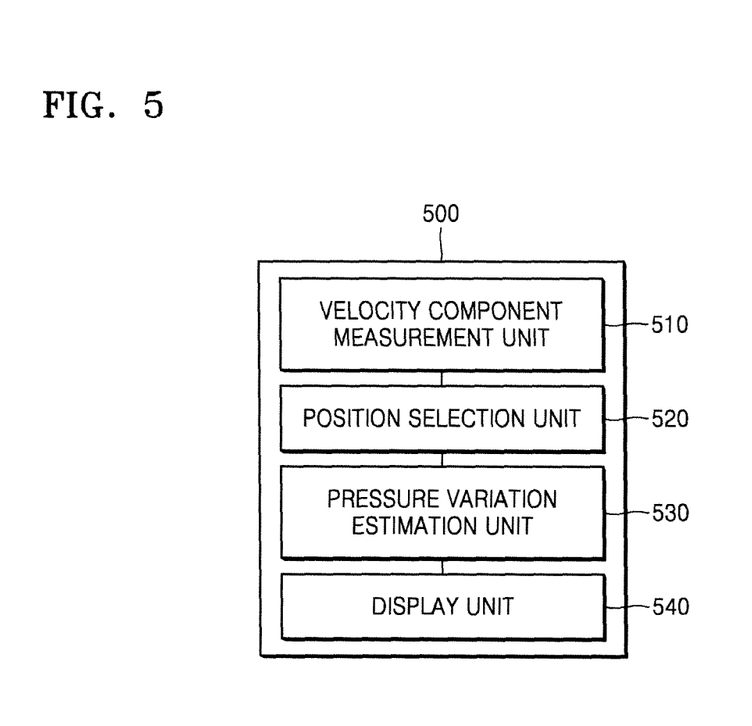
FIG. 5 is a block diagram illustrating an apparatus for representing a relative pressure variation in an object, according to an embodiment of the present invention.

FIG. 5 is a block diagram illustrating an apparatus 500 for representing a relative pressure variation in an object on an image of the object, according to an embodiment of the present invention.

The apparatus 500 for representing the pressure variation in the object on the image of the object, according to the embodiment of the present invention, may include a velocity component measurement unit 510 that measures all velocity components of the object, a position selection unit 520 that selects a first position on an image of the object, a pressure variation estimation unit 530 that estimates a pressure variation between the first position and a second position that is separate from the selected first position, and a display unit 540 that displays the estimated pressure variation on the image of the object by using a predetermined indicator.

According to the embodiment of the present invention, the object may be a blood vessel or a heart. The velocity component measurement unit 510 may acquire velocity components at respective positions of the interior of the object. The velocity component measurement unit 510 may acquire velocity components at respective positions of the interior of the object by using plane waves. In order words, all velocity components of the object may be acquired at respective positions of the interior of the object by using the plane waves at one time. According to the embodiment of the present invention, the velocity components for the object are acquired at one time by using plane waves, and a relative pressure at a point or region of the object may be estimated based on the acquired velocity components, thus quickly and precisely estimating a relative pressure of the object.

The first position may be a predetermined point or region of the interior of the object.

According to the embodiment of the present invention, the pressure variation estimation unit 530 may estimate a pressure variation value Δp at the second position with respect to the first position, based on the velocity component at the first position and the velocity component at the second position.

According to the embodiment, the pressure variation value Δp may be estimated by using $\Delta P = 4*(v_2^2 - v_1^2)$.

According to the embodiment of the present invention, the predetermined indicator may include at least one of characters, numbers, symbols, colors, graphs, and images.

The above-described methods may apply to an apparatus according to an embodiment of the present invention, and thus, repeated descriptions of thereof are omitted.

The embodiments of the present invention may be written as computer programs and may be implemented in general-use digital computers that execute the programs by using a computer-readable recording medium.

Examples of the computer-readable recording mediums may include recording mediums such as magnetic storage mediums (e.g., ROM, floppy disks, hard disks, etc.), and optical recording mediums (e.g., CD-ROMs, DVDs, etc.).

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of representing a pressure variation in an object on an image of the object, the method comprising:
    measuring, by a velocity component measurement unit, multiple velocity components of the object by acquiring concurrently the velocity components at each respective position of respective positions of an inner part of the object by using plane waves;
    selecting, by a position selection unit, a first position on the image of the object;
    determining, by a pressure variation estimation unit, a velocity component at the first position and a velocity component at a second position which is separate from the selected first position by a predetermined distance, based on the measured velocity components of the object;
    estimating, by the pressure variation estimation unit, a pressure variation between the first position and the second position by using the determined velocity component at the first position and the determined velocity component at the second position; and
    displaying, on a display, the estimated pressure variation on the image of the object by using a predetermined indicator,
    wherein the displaying the estimated pressure variation on the image comprises representing the estimated pressure variation at the second position with respect to the first position through a predetermined color by using a color bar in which different colors are assigned depending on the pressure variation.

2. The method of claim 1, wherein the object is a blood vessel or a heart.

3. The method of claim 1, wherein the first position is a predetermined point or region of an interior of the object.

4. The method of claim 3, wherein the estimating of a pressure variation between the first position and the second position that is separate from the selected first position comprises estimating a pressure variation value ($\Delta p$) at the second position with respect to the first position by a predetermined distance, based on the velocity component at the first position and the velocity component at the second position.

5. The method of claim 4, wherein the pressure variation value $\Delta p$ is estimated by using $\Delta P=4*(v_2^2-v_1^2)$.

6. The method of claim 1, wherein the predetermined indicator includes at least one of characters, numbers, symbols, colors, graphs, and images.

7. The method of claim 1, wherein the displaying of the estimated pressure variation on the image comprises:
    representing the estimated pressure variation at the second position with respect to the first position through a predetermined color by using a color bar in which different colors are assigned depending on the pressure variation; and
    displaying, at the second position, a numerical value of the estimated pressure variation at the second position with respect to the first position.

8. A computer-readable recording medium that stores a program, which, when executed by a computer, performs the method of claim 1.

9. An apparatus for representing a pressure variation in an object on an image of the object, the apparatus comprising:
    a velocity component measurement unit configured to measure multiple velocity components of the object by acquiring concurrently the velocity components at each respective position of respective positions of an inner part of the object by using plane waves;
    a position selection unit configured to select a first position on the image of the object;
    a pressure variation estimation unit configured to determine a velocity component at a second position which is separate from the selected first position by a predetermined distance based on the measured velocity components of the object, and to estimate a pressure variation between the first position and the second position by using a measured velocity component at the first position and the determined velocity component at the second position; and
    a display configured to display the estimated pressure variation on the image of the object by using a predetermined indicator,
    wherein the display is further configured to display the estimated pressure variation at the second position with respect to the first position through a predetermined color by using a color bar in which different colors are assigned depending on the pressure variation.

10. The apparatus of claim 9, wherein the object is a blood vessel or a heart.

11. The apparatus of claim 9, wherein the first position is a predetermined point or region of an interior of the object.

12. The apparatus of claim 11, wherein the pressure variation estimation unit is further configured to estimate a pressure variation value ($\Delta p$) at the second position with respect to the first position, based on the velocity component at the first position and the velocity component at the second position.

13. The apparatus of claim 12, wherein the pressure variation value tip is estimated by using $\Delta P=4*(v_2^2-v_1^2)$.

14. The apparatus of claim 9, wherein the predetermined indicator includes at least one of characters, numbers, symbols, colors, graphs, and images.

15. The apparatus of claim 9, wherein the displaying of the estimated pressure variation on the image comprises:
    representing the estimated pressure variation at the second position with respect to the first position through a predetermined color by using a color bar in which different colors are assigned depending on the pressure variation; and
    displaying, at the second position, a numerical value of the estimated pressure variation at the second position with respect to the first position.

* * * * *